US012564824B2

(12) United States Patent
Pettersson et al.

(10) Patent No.: US 12,564,824 B2
(45) Date of Patent: Mar. 3, 2026

(54) PRE-HYDROLYSIS PRESSURE VESSEL SYSTEM COMPRISING A CLEANING ARRANGEMENT

(71) Applicant: VALMET AB, Sundsvall (SE)

(72) Inventors: Patrik Pettersson, Alnö (SE); Lars Fredriksson, Alnö (SE); Christer Hägglund, Bergeforsen (SE)

(73) Assignee: VALMET AB, Sundsvall (SE)

( * ) Notice: Subject to any disclaimer, the term of this patent is extended or adjusted under 35 U.S.C. 154(b) by 596 days.

(21) Appl. No.: 18/008,858

(22) PCT Filed: May 10, 2021

(86) PCT No.: PCT/SE2021/050436
§ 371 (c)(1),
(2) Date: Dec. 7, 2022

(87) PCT Pub. No.: WO2021/251861
PCT Pub. Date: Dec. 16, 2021

(65) Prior Publication Data
US 2023/0256411 A1      Aug. 17, 2023

(30) Foreign Application Priority Data
Jun. 8, 2020    (SE) .................................. 2050666-3

(51) Int. Cl.
*B01J 19/20*        (2006.01)
*B65G 33/24*        (2006.01)
(Continued)

(52) U.S. Cl.
CPC .............. *B01J 19/20* (2013.01); *B65G 33/24* (2013.01); *B65G 45/005* (2013.01); *C10L 5/40* (2013.01);
(Continued)

(58) Field of Classification Search
CPC ........................... B01J 19/20; B01J 2219/182; B01J 2219/185; B65G 45/005
See application file for complete search history.

(56) References Cited

U.S. PATENT DOCUMENTS 7,081,171 B1      7/2006  Sabol et al.
2011/0114570 A1*   5/2011  Hojsgaard ............... C02F 11/18
                                                210/199
(Continued)

FOREIGN PATENT DOCUMENTS

CN        105539894 A      5/2016
CN        108393057 A      8/2018
(Continued)

OTHER PUBLICATIONS

Extended European Search Report issued in connection with EP Appl. No. 21820891.6 on Oct. 10, 2023.

*Primary Examiner* — Lessanework Seifu
(74) *Attorney, Agent, or Firm* — Foley & Lardner LLP

(57)        ABSTRACT
A pre-hydrolysis pressure vessel system includes; a material inlet for receiving biomass material to be treated in the pre-hydrolysis pressure vessel system and a material outlet for expelling treated biomass material out from the pre-hydrolysis pressure vessel system; a transport screw arrangement including a transport screw provided inside an enclosing housing of the transport screw arrangement, said transport screw being configured for transporting biomass material through the enclosing housing towards the material outlet of the pre-hydrolysis pressure vessel system. The enclosing housing includes a cleaning arrangement that includes: at least one elongated fluid channel positioned in connection with an inner wall of the enclosing housing and wherein said at least one elongated fluid channel comprises a number of fluid outlets, and at least one cleaning fluid inlet
(Continued)

which is provided through the enclosing housing in fluid connection with the at least one fluid channel.

11 Claims, 5 Drawing Sheets

(51) Int. Cl.
| | | |
|---|---|---|
| B65G 45/00 | (2006.01) |
| C10L 5/40 | (2006.01) |
| D21B 1/02 | (2006.01) |
| D21C 1/02 | (2006.01) |

(52) U.S. Cl.
CPC ................. *D21B 1/02* (2013.01); *D21C 1/02* (2013.01); *C12P 2201/00* (2013.01)

(56) References Cited

U.S. PATENT DOCUMENTS

| | | | | |
|---|---|---|---|---|
| 2020/0306719 A1* | 10/2020 | Lambert | .................. | C13K 1/02 |
| 2020/0346222 A1* | 11/2020 | Pettersson | ............... | B01J 19/20 |

FOREIGN PATENT DOCUMENTS

| | | | |
|---|---|---|---|
| EP | 3 399 095 A1 | 11/2018 |
| JP | 055720 U | 1/1993 |
| WO | WO-2010/081476 A1 | 7/2010 |
| WO | WO-2019/088906 A1 | 5/2019 |
| WO | WO-2019/103674 A1 | 5/2019 |
| WO | WO-2019/209153 A1 | 10/2019 |
| WO | WO-2020/040677 A1 | 2/2020 |

* cited by examiner

PRE-HYDROLYSIS PRESSURE VESSEL SYSTEM COMPRISING A CLEANING ARRANGEMENT

TECHNICAL FIELD OF THE INVENTION

The present invention relates to a pre-hydrolysis pressure vessel system comprising a cleaning arrangement.

BACKGROUND

In pre-hydrolysis pressure vessel systems for treating biomass precipitation is build up and may cause problems. The precipitation may stick to for example inner walls and to a transport screw arranged for transporting the biomass through the system. The precipitation may cause friction and may affect the material transport efficiency. Pieces of precipitation material can come loose and cause problems downstream in the system.

SUMMARY

An object of the present invention is to provide a pre-hydrolysis pressure vessel system in which precipitation effectively can be removed.

This is achieved in a pre-hydrolysis pressure vessel system according to claim 1.

According to one aspect of the invention a pre-hydrolysis pressure vessel system comprising a material inlet for receiving biomass material to be treated in the pre-hydrolysis pressure vessel system and a material outlet for expelling treated biomass material out from the pre-hydrolysis pressure vessel system is provided, wherein said pre-hydrolysis pressure vessel system further comprises a transport screw arrangement, said transport screw arrangement comprising a transport screw provided inside an enclosing housing of the transport screw arrangement, said transport screw being configured for transporting biomass material through the enclosing housing towards the material outlet of the pre-hydrolysis pressure vessel system, wherein said enclosing housing comprises a cleaning arrangement, said cleaning arrangement comprising at least one elongated fluid channel provided along at least a part of a length, L1 of the enclosing housing and positioned in connection with an inner wall of the enclosing housing and wherein said at least one elongated fluid channel comprises a number of fluid outlets separated along a length, L2, of the at least one fluid channel, wherein said cleaning arrangement further comprises at least one cleaning fluid inlet which is provided through the enclosing housing in fluid connection with the at least one fluid channel whereby a cleaning fluid can be provided into the enclosing housing from outside the enclosing housing, via the cleaning fluid inlet and through the at least one fluid channel and said fluid outlets for cleaning the transport screw and/or the inner wall of the enclosing housing.

Hereby a pre-hydrolysis pressure vessel system is achieved in which cleaning fluid can be transferred through a cleaning fluid inlet from outside the enclosing housing into the enclosing housing via at least one fluid channel and further via a number of fluid outlets which are separated along the length of the fluid channel. Hereby a cleaning fluid can be provided inside the enclosing housing at different positions along a length of the enclosing housing without the need to provide separate fluid connections from outside the enclosing housing to each of the fluid outlets. Hereby both the construction of and the handling of the pre-hydrolysis vessel is improved. By providing cleaning fluid at a number of different positions within the enclosing housing precipitation can be flushed off effectively. Suitably the precipitation is removed while it is still soft and not heavily stuck to inner walls of the enclosing housing and/or to the transport screw.

In some embodiments of the invention said cleaning arrangement comprises at least two fluid channels positioned separated around the circumference of the inner wall of the enclosing housing. Hereby cleaning may be more effective and a larger surface area o the inner wall may be reached by cleaning fluid.

In some embodiments of the invention the enclosing housing is separated into at least two different cleaning sections along its length, L1, where each cleaning section comprises at least one fluid channel and wherein at least one cleaning fluid inlet is provided to each cleaning section. Hereby cleaning of the different cleaning sections of the enclosing housing and/or the transport screw can be performed in different cycles, i.e. different parts of the transport screw arrangement can be cleaned at different times.

In some embodiments of the invention each fluid channel is provided inside an anti-rotation bar in the enclosing housing. Hereby a space efficient solution is provided.

In some embodiments of the invention the cleaning arrangement comprises at least one elongated bar which is connected to the inner wall of the enclosing housing and which elongated bar encloses said at least one fluid channel.

In some embodiments of the invention the at least one elongated bar is in the form of a U- or V-profile which is connected to the inner wall of the enclosing housing such that the at least one fluid channel of the cleaning arrangement is provided between the inner wall of the enclosing housing and the at least one elongated bar.

In some embodiments of the invention at least some of the fluid outlets are provided with an opening being at least 10 times wider than its height and wherein a height of at least some of the fluid outlets is between 0,05-1.5 mm or between 0,05-1 mm. Hereby a high velocity of the cleaning fluid can be achieved which will assure a high impact energy and an effective cleaning.

In some embodiments of the invention the fluid outlets comprise both perpendicular fluid outlets and tangential fluid outlets, wherein the perpendicular fluid outlets are positioned such that fluid is delivered out from the at least one fluid channel via the perpendicular fluid outlets in a perpendicular direction to the inner wall and the tangential fluid outlets are positioned such that fluid is delivered out from the at least one fluid channel via the tangential fluid outlet in a tangential direction to the inner wall. Hereby both the inner wall of the enclosing housing and the transport screw can be effectively cleaned.

In some embodiments of the invention the pre-hydrolysis pressure vessel comprises a horizontal bioreactor.

In some embodiments of the invention the pre-hydrolysis pressure vessel comprises a vertical bioreactor and a horizontal transport screw arrangement for transporting biomass out from the vertical bioreactor towards the material outlet of the pre-hydrolysis pressure vessel, wherein said cleaning arrangement is provided in said horizontal transport screw arrangement.

In some embodiments of the invention anti-rotation bars provided in the enclosing housing are designed to comprise said at least one fluid channels and said fluid outlets.

DETAILED DESCRIPTION OF EMBODIMENTS

Figure 1A:
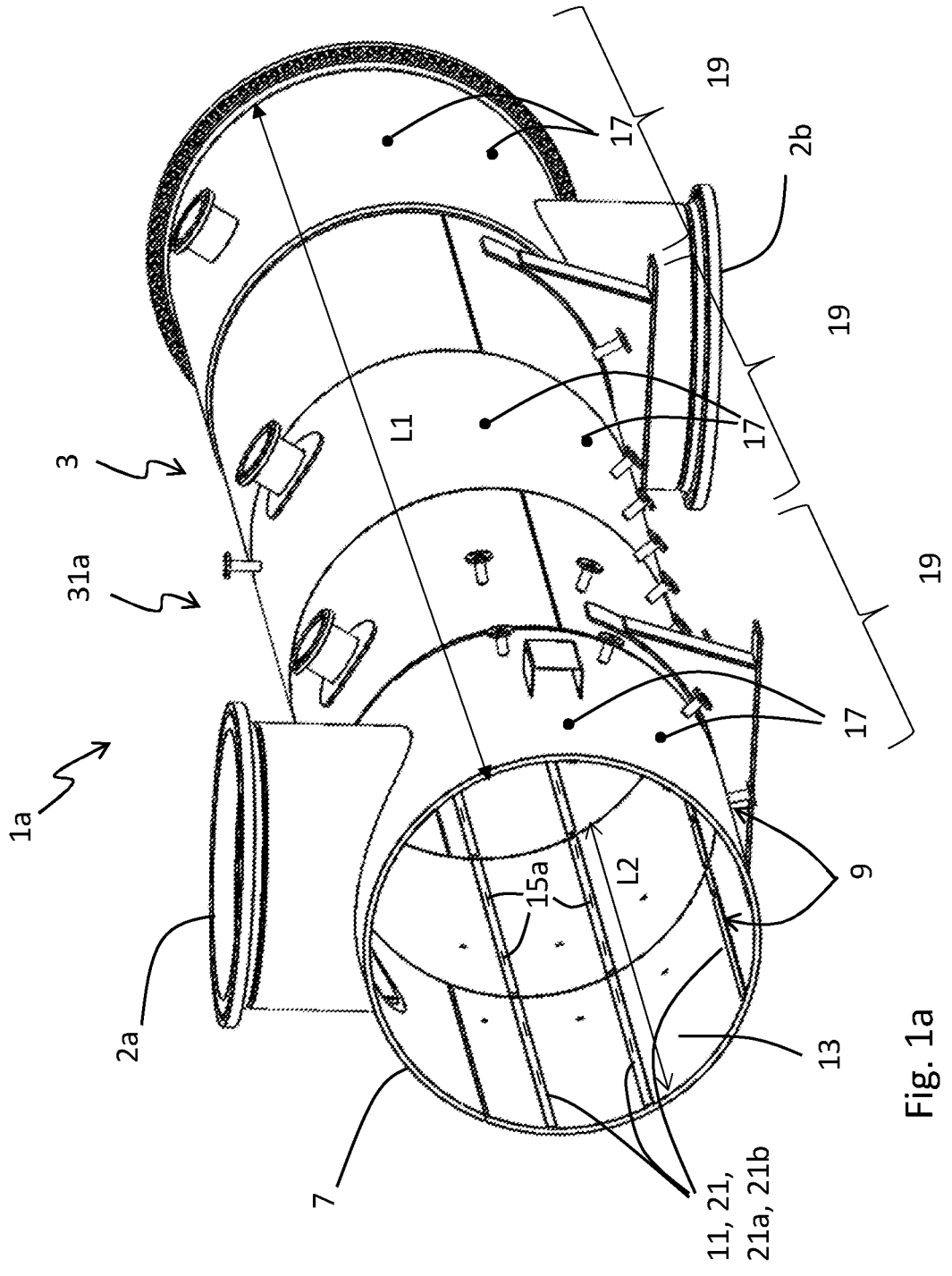
FIG. 1a shows schematically parts of a pre-hydrolysis pressure vessel system comprising a horizontal bioreactor provided with a cleaning arrangement according to one embodiment of the invention.
Figure 1B:
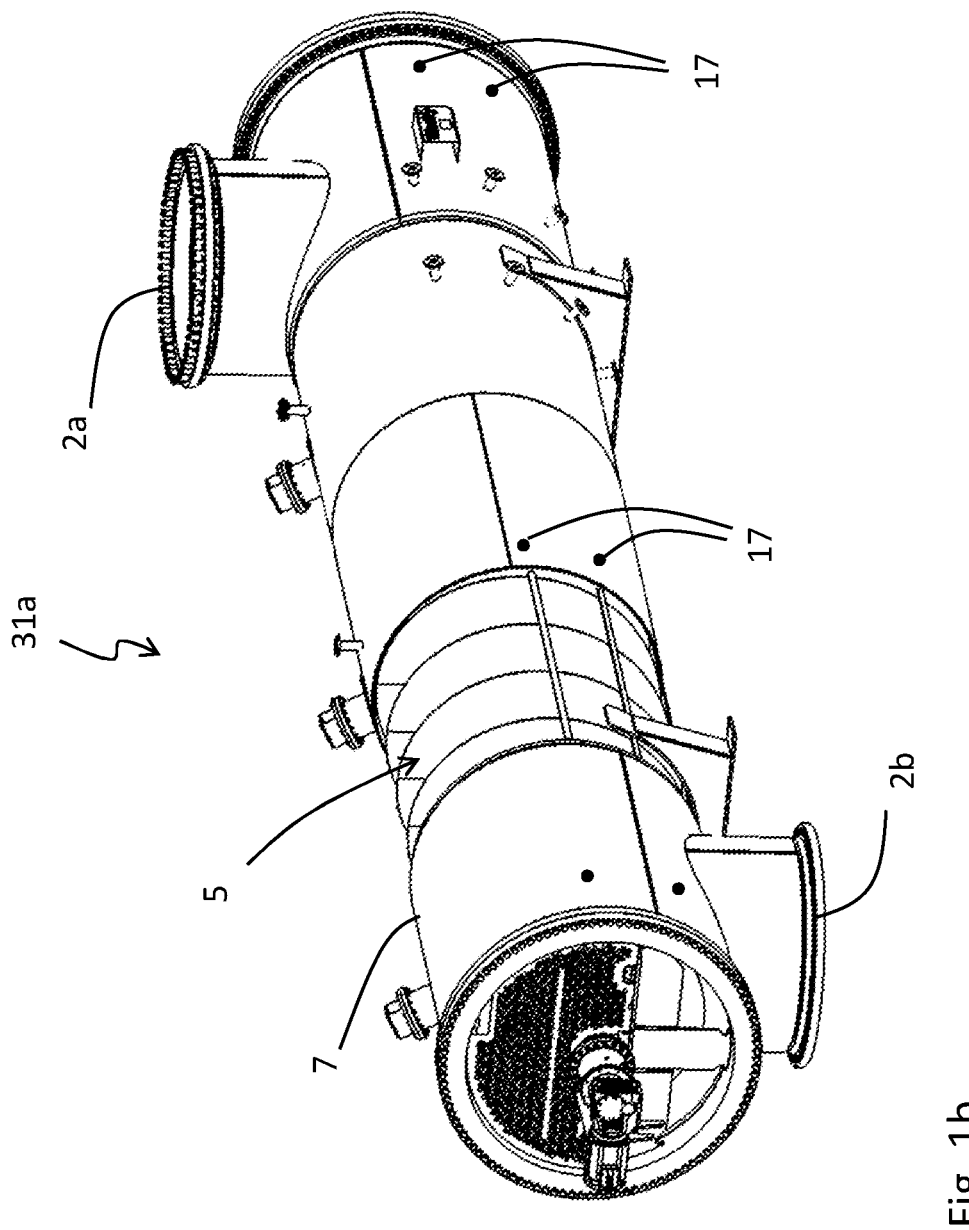
FIG. 1b shows schematically the same pre-hydrolysis pressure vessel system as shown in FIG. 1a from the other side and comprising a transport screw.

FIG. 1a shows schematically parts of a pre-hydrolysis pressure vessel system 1a comprising a horizontal bioreactor 31a provided with a cleaning arrangement 9 according to one embodiment of the invention. In FIG. 1a a transport screw normally provided within the horizontal bioreactor 31a is removed for allowing free sight of an inner wall 13 of an enclosing housing 7 of the horizontal bioreactor 31b. FIG. 1b shows schematically the same pre-hydrolysis pressure vessel system 1a as shown in FIG. 1a but from the other side and comprising a transport screw 5 which can be seen in a middle section where a part of the enclosing housing 7 has been removed.

Figure 1C:
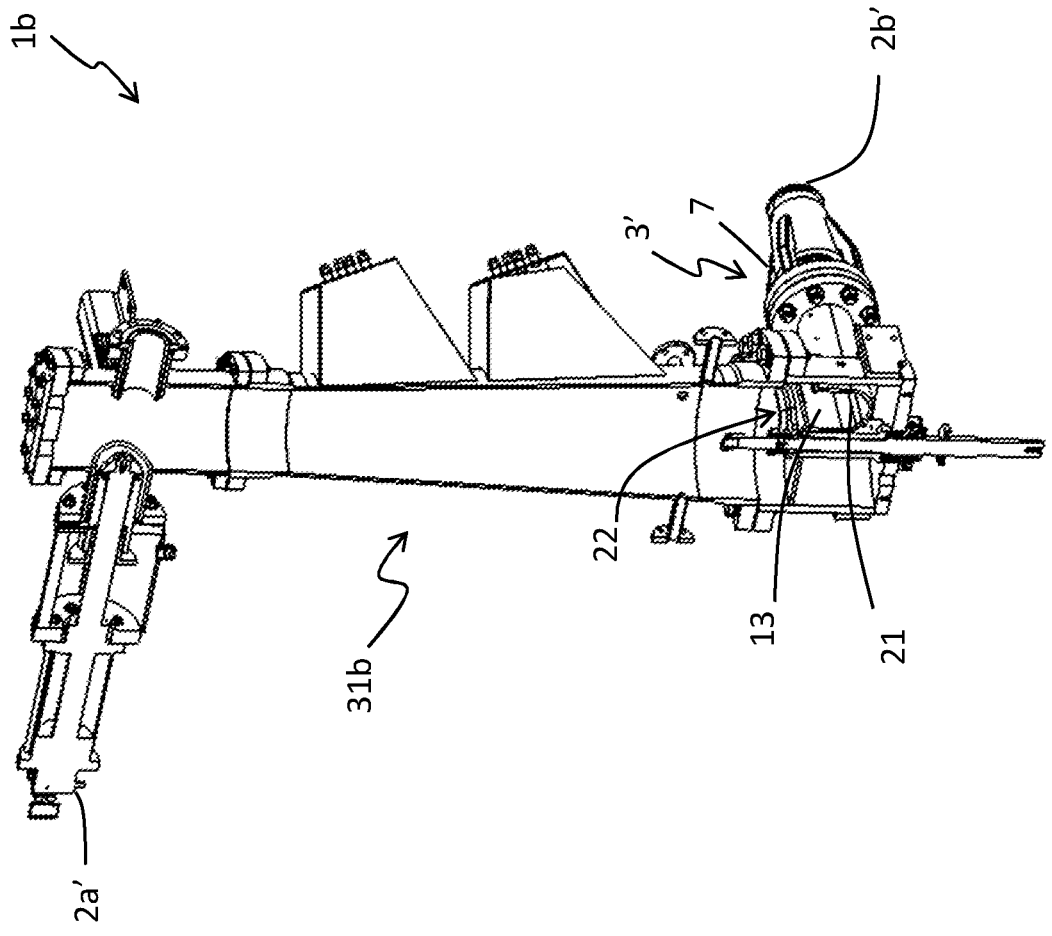
FIG. 1c shows schematically parts of a pre-hydrolysis pressure vessel system comprising a vertical bioreactor which can be provided with a cleaning arrangement according to the invention.

FIG. 1c shows schematically parts of a pre-hydrolysis pressure vessel system 1b comprising a vertical bioreactor 31b. This pre-hydrolysis pressure vessel system 1b comprises a transport screw arrangement 3' connected to a bioreactor outlet 22 of the vertical bioreactor 31b for transporting material out from the vertical bioreactor 31b towards a material outlet 2b' of the whole pre-hydrolysis pressure vessel system 1b. The transport screw arrangement 3' can be provided with a cleaning arrangement 9 according to the invention.

Figure 2A:
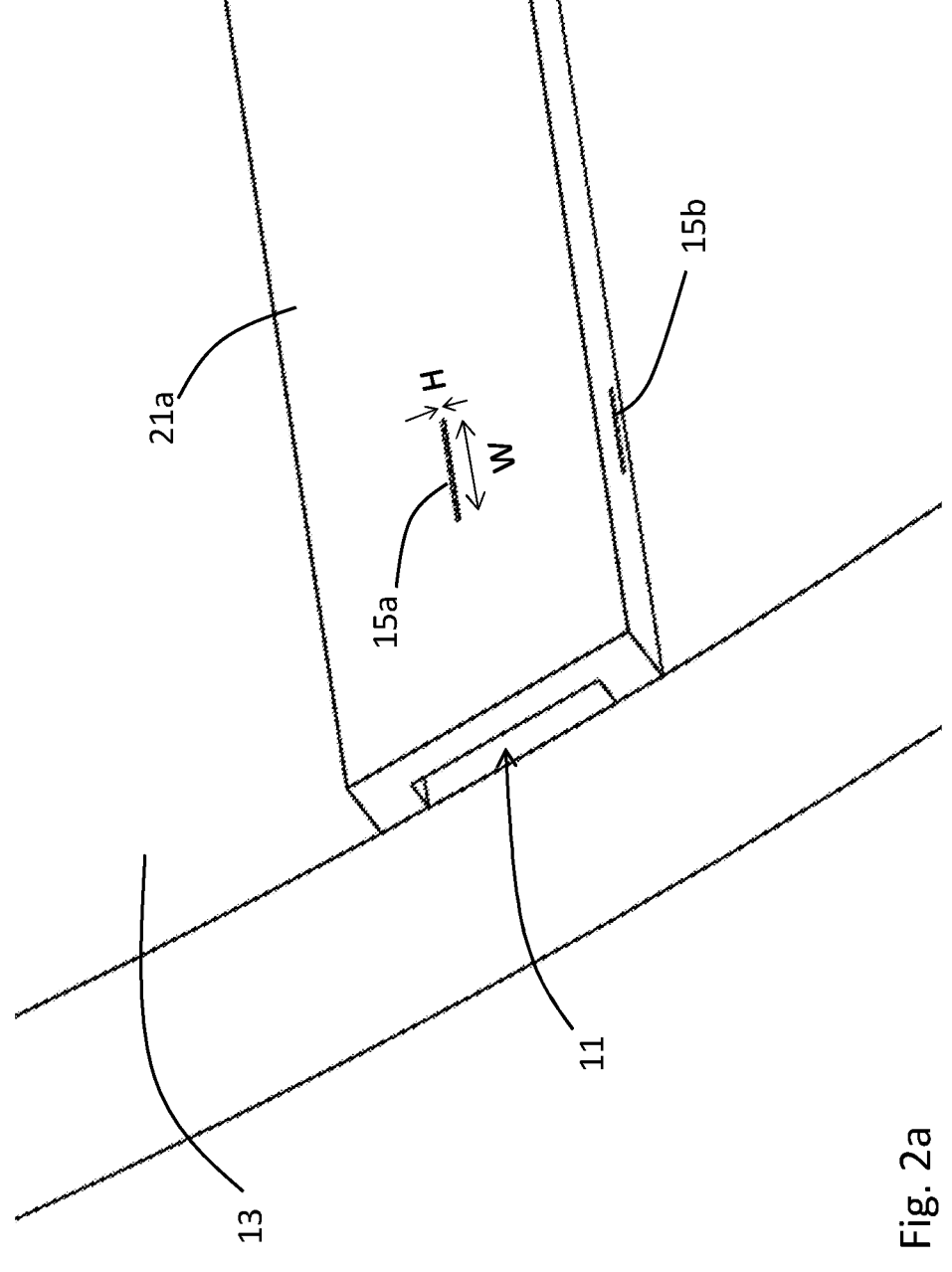
FIG. 2a shows schematically parts of a cleaning arrangement according to one embodiment of the invention.

FIG. 2a shows schematically parts of a cleaning arrangement 9 according to one embodiment of the invention, which cleaning arrangement 9 can be provided to both of the transport screw arrangements 3; 3' of the two different types of pre-hydrolysis pressure vessel systems 1a; 1b as shown in FIGS. 1a-1c.

Figure 2B:
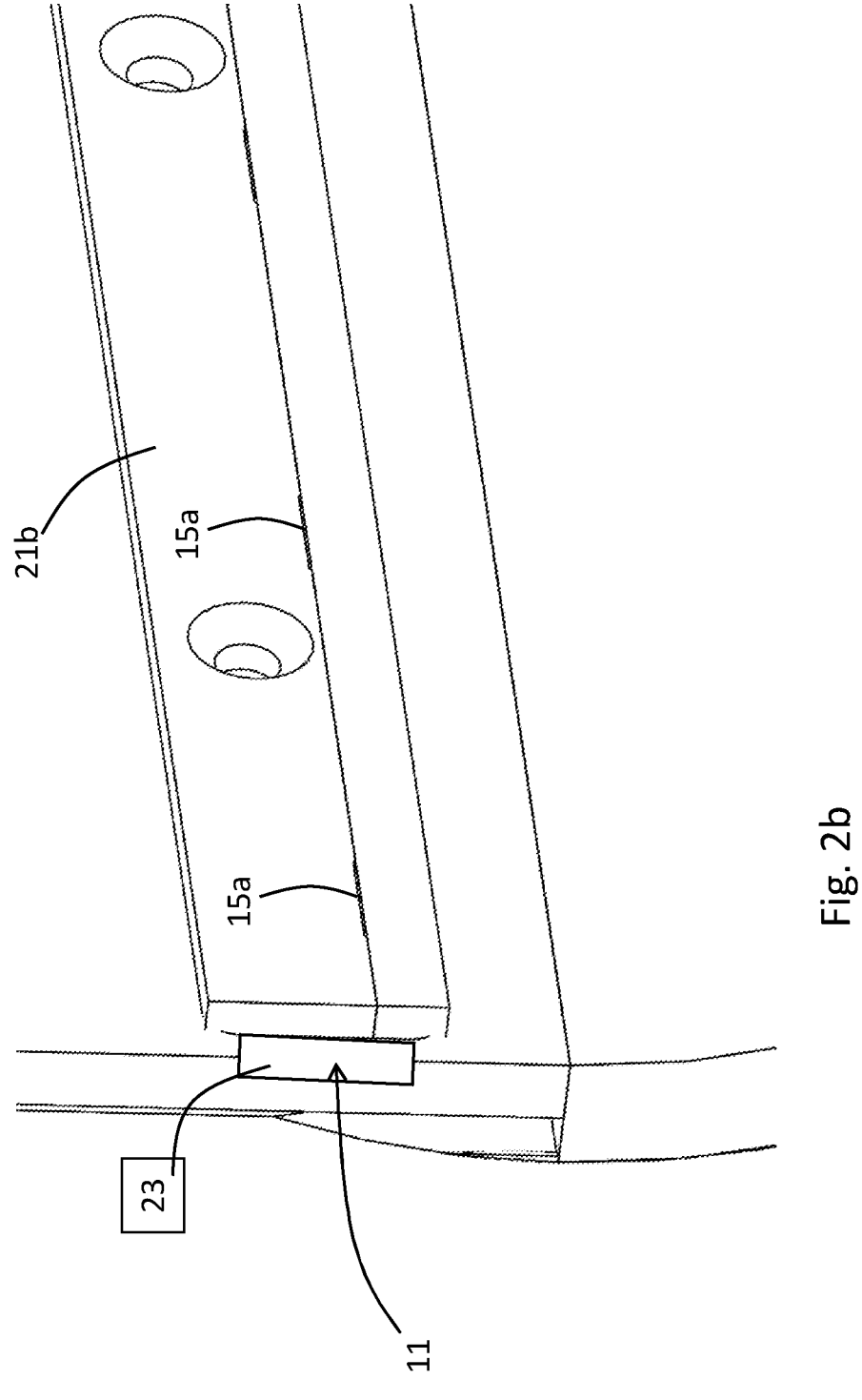
FIG. 2b shows schematically parts of a cleaning arrangement according to another embodiment of the invention.

FIG. 2b shows schematically an alternative design of a cleaning arrangement 9 according to one embodiment of the invention.

The invention will now be described with reference to all the Figures.

According to the invention a pre-hydrolysis pressure vessel system 1a; 1b comprising a cleaning arrangement 9 is provided. The pre-hydrolysis pressure vessel system 1a; 1b can comprise either a horizontal bioreactor 31a as shown in FIGS. 1a-1b or a vertical bioreactor 31b as shown in FIG. 1c. The cleaning arrangement 9 is in both cases provided to a transport screw arrangement 3; 3'provided in the pre-hydrolysis pressure vessel system 1a; 1b. For the pre-hydrolysis pressure vessel system 1a comprising a horizontal bioreactor 31a the transport screw arrangement 3 is provided within the bioreactor itself, i.e. the treating of the material is performed during transport of the material in the transport screw arrangement 3. For the pre-hydrolysis pressure vessel system 1b comprising a vertical bioreactor 31b the transport screw arrangement 3' is provided connected to a bioreactor outlet 22 of the vertical bioreactor 31b for transporting biomass material our from the vertical bioreactor 31b.

The pre-hydrolysis pressure vessel system 1a; 1b comprises a material inlet 2a; 2a' for receiving biomass material to be treated in the pre-hydrolysis pressure vessel system 1a; 1b and a material outlet 2b; 2b' for expelling treated biomass material out from the pre-hydrolysis pressure vessel system 1a; 1b. Said pre-hydrolysis pressure vessel system 1a; 1b comprises further a transport screw arrangement 3; 3' as described above. The transport screw arrangement 3; 3' comprises a transport screw 5 provided inside an enclosing housing 7 and said transport screw 5 is configured for transporting biomass material through the enclosing housing 7 towards the material outlet 2b; 2b' of the pre-hydrolysis pressure vessel system 1a; 1b.

According to the invention said enclosing housing 7 comprises a cleaning arrangement 9. Said cleaning arrangement 9 comprises at least one elongated fluid channel 11 which is provided along at least a part of a length, L1, of the enclosing housing 7. The at least one elongated fluid channel 11 is positioned in connection with an inner wall 13 of the enclosing housing 7. Said at least one elongated fluid channel 11 comprises a number of fluid outlets 15a, 15b separated along a length, L2, of the at least one fluid channel 11. The cleaning arrangement 9 comprises further at least one cleaning fluid inlet 17 which is provided through the enclosing housing 7 in fluid connection with the at least one fluid channel 11 whereby a cleaning fluid can be provided into the enclosing housing 7 from outside the enclosing housing, via the cleaning fluid inlet 17 and through the at least one fluid channel 11 and said fluid outlets 15a, 15b for cleaning of the transport screw 5 and/or the inner wall 13 of the enclosing housing 7, i.e. for removing of precipitation. Hereby cleaning fluid will be distributed via the fluid channel 11 to more than one fluid outlets 15a, 15b. Hereby the number of cleaning fluid inlets 17 can be decreased compared to prior art systems where many separate nozzles are provided through the enclosing housing 7 for providing cleaning fluid into the enclosing housing.

In one embodiment of the invention only one fluid channel 11 is provided to the enclosing housing 7, which fluid channel 11 may be provided along substantially the whole length, L1, of the enclosing housing 7. However, in order to improve cleaning efficiency, especially of the inner wall 13, more than one fluid channels 11 may be provided. The cleaning arrangement 9 may comprise two or more fluid channels 11 which are positioned separated around a circumference of the inner wall 13 of the enclosing housing 7. Hereby the cleaning will be more efficient and a larger part of the inner wall 13 can be reached with the cleaning fluid. In the pre-hydrolysis pressure vessel system of FIG. 1a, five fluid channels 11 are provided separated around the circumference of the inner wall 13, whereof three fluid channels 11 can be seen in this view. However, less or more than five fluid channels 11 may also be provided. In the embodiment of the invention shown in FIG. 1a the fluid channels 11 are also separated into different cleaning sections 19. The enclosing housing 7 and the fluid channels 11 are in this embodiment separated into three different cleaning sections 19 along the length, L1, of the enclosing housing. Each cleaning section 19 comprises at least one fluid channel 11 (five fluid channels 11 are provided in each cleaning section 19 in the embodiment shown in FIG. 1a). At least one cleaning fluid inlet 17 is provided to each cleaning section 19 (in the embodiment shown in FIG. 1a one fluid inlet 17 is provided for each fluid channel 11 in each cleaning section 19, i.e. five fluid inlets 17 are provided in each cleaning section, whereof two fluid inlets 17 can be seen in this view for each cleaning section 19). The number of cleaning sections 19 can however be different than three, for example two, four or more. By separating the enclosing housing 7 into different cleaning sections 19 each cleaning section 19 can be treated separately, i.e. cleaning fluid can be provided separately and at different times and different amounts to the different cleaning sections 19. This may be suitable because in some applications the volume of cleaning fluid added into the enclosing housing 7 needs to be kept low in order not to overly dilute the biomass material which is transported in the transport screw arrangement 3. By providing cleaning fluid only to one section 19 at the time the speed of flow of cleaning fluid may also be kept higher and may therefore be more effective for cleaning than if the whole length of the enclosing house 7 would have to be cleaned at the same time.

In another embodiment of the invention however the whole length, or substantially the whole length, of the enclosing housing 7 can be cleaned at the same time. Furthermore, in some embodiments the amount of cleaning fluid may not need to be kept low because the biomass material provided inside the enclosing housing can be discarded after the cleaning. However, if biomass material should not be wasted cyclic cleaning in cleaning sections 19 may be preferred. In some embodiments of the invention each fluid channel 11 is provided inside an anti-rotation bar 21 in the enclosing housing 7. Anti-rotation bars are often provided in transport screw arrangements for decreasing a risk that the material is rotated inside the enclosing housing 7 and not transported along the enclosing housing 7 as wanted. By providing the fluid channels 11 inside these anti-rotation bars 21 a space efficient solution is provided.

The cleaning arrangement 9 may comprise at least one elongated bar 21a, 21b which is connected to the inner wall 13 of the enclosing housing 7 and which encloses the at least one fluid channel 11 of the cleaning arrangement 9. This elongated bar 21a, 21b may also work as anti-rotation bar in the transport screw arrangement 3; 3' as described above. In other words, anti-rotation bars 21 provided in the enclosing housing 7 can be designed to comprise said at least one fluid channel 11 and said fluid outlets 15a, 15b.

Two different embodiments of elongated bars 21a, 21b are shown in FIGS. 2a and 2b. In the embodiment shown in FIG. 2a the at least one bar 21a is in the form of a U- or V-profile which is connected to the inner wall 13 of the enclosing housing 7 such that the at least one fluid channel 11 of the cleaning arrangement 9 is provided between the inner wall 13 of the enclosing housing 7 and the at least one bar 21a.

In the embodiment shown in FIG. 2b the cleaning arrangement 9 further comprises at least one elongated groove 23 provided in the inner wall 13 of the enclosing housing 7, which at least one groove 23 is covered by at least one elongated bar 21b comprising the fluid outlets 15a of the at least one fluid channel 11, whereby said at least one fluid channel 11 is provided in said at least one groove 23.

The fluid outlets 15a, 15b can be seen in FIGS. 1a, 2a and 2b, In some embodiments of the invention, as shown in FIG. 2a, the fluid outlets 15a, 15b comprise both perpendicular fluid outlets 15a and tangential fluid outlets 15b, wherein the perpendicular fluid outlets 15a are positioned such that fluid is delivered out from the at least one fluid channel 11 via the perpendicular fluid outlets 15a in a perpendicular direction to the inner wall 13 and the tangential fluid outlets 15b are positioned such that fluid is delivered out from the at least one fluid channel 11 via the tangential fluid outlet 15b in a tangential direction to the inner wall 13. In some embodiment the perpendicular fluid outlets 15a and the tangential fluid outlets 15b can be provided to different fluid channels 11, i.e. such that at least one fluid channel 11 comprises only perpendicular fluid outlets 15a and at least one other fluid channel 11 comprises only tangential fluid outlets 15b. Hereby cleaning can be done separately for the inner wall (by use of the tangential fluid outlets 15b) and the transport screw wall (by use of the perpendicular fluid outlets 15a). Hereby a fluid volume can be controlled and kept low in order not to dilute the biomass material more than necessary. In another embodiment however both perpendicular and tangential fluid outlets 15a, 15b are provided to the same fluid channels 11, as shown in FIG. 2a. In still another embodiment only perpendicular or only tangential fluid outlets 15a, 15b are provided to the at least one fluid channel 11. In FIG. 2a the tangential fluid outlets 15b can only be seen on one side of the bar 21a, however tangential fluid outlets can also be provided on the other side of the bar 21a.

In order to provide efficient cleaning of the inner wall 13 and/or the transport screw 5, i.e. removal of precipitation from the inner wall 13 and/or the transport screw 5, a high speed of the cleaning fluid flow out from the fluid outlets 15a, 15b is suitable. However, as discussed above the volume of used cleaning fluid should be kept low in order not to dilute the biomass material more than necessary. For providing a high flow speed and a good cleaning effect of the cleaning fluid the dimensions of the fluid outlets 15a, 15b can be optimised. A height, H, of the fluid outlets 15a, 15b is according to some embodiments of the invention kept as small as possible, while a width/length, W, of the fluid outlets 15a, 15b can be provided much larger.

The width/length, W, of the fluid outlets 15a, 15b is provided along the length of the fluid channels 11 and a larger width/length will increase the cleaning area inside the enclosing housing 7, i.e. a larger part of the inner walls 13 and/or the transport screw will be cleaned if the fluid outlets 15a, 15b have a larger width/length along the length, L2, of the fluid channels 11. The height, H, of the fluid channels 15a, 15b should be kept as small as possible, and can be for example 0,05-1.5 mm or 0,05-1 mm while the width/length of the fluid outlets 15a, 15b may be 10 times larger or more.

The invention claimed is:

1. A pre-hydrolysis pressure vessel system comprising:
   a material inlet for receiving biomass material to be treated in the pre-hydrolysis pressure vessel system;
   a material outlet for expelling treated biomass material out from the pre-hydrolysis pressure vessel system; and
   a transport screw arrangement comprising:
      an enclosing housing;
      at least one anti-rotation bar provided in the enclosing housing and configured to decrease a risk that the material is rotated inside the enclosing housing, and
      a transport screw provided in the enclosing housing, said transport screw being configured for transporting biomass material through the enclosing housing towards the material outlet of the pre-hydrolysis pressure vessel system,
   wherein said enclosing housing comprises a cleaning arrangement, said cleaning arrangement comprising:
      at least one elongated fluid channel provided along at least a part of a length (L1) of the enclosing housing, each defined by an inner wall of the enclosing housing and a respective anti-rotation bar, wherein each elongated fluid channel comprises a plurality of fluid outlets provided in the respective anti-rotation bar and separated along a length (L2) of the respective fluid channel, and
      at least one cleaning fluid inlet which is provided through the enclosing housing in fluid connection with the at least one fluid channel whereby a cleaning fluid can be provided into the enclosing housing from outside the enclosing housing, via the cleaning fluid inlet and through the at least one fluid channel and said fluid outlets for cleaning the transport screw and/or the inner wall of the enclosing housing.

2. The pre-hydrolysis pressure vessel system according to claim 1, wherein:

the at least one anti-rotation bar comprises at least two anti-rotation bars positioned around a circumference of the inner wall of the enclosing housing, and said at least one fluid channel comprises at least two fluid channels, each defines by the inner wall of the enclosing housing and a respective anti-rotation bar.

3. The pre-hydrolysis pressure vessel system according to claim 1, wherein the enclosing housing is separated into at least two different cleaning sections along its length (L1) where each cleaning section comprises at least one fluid channel, and at least one cleaning fluid inlet is provided to each cleaning section.

4. The pre-hydrolysis pressure vessel system according to claim 1, wherein each anti-rotation bar has a U- or V-profile.

5. The pre-hydrolysis pressure vessel system according to claim 1, wherein at least some of the fluid outlets are provided with an opening being at least 10 times wider than its height and a height of at least some of the fluid outlets is between 0.05-1 mm.

6. The pre-hydrolysis pressure vessel system according to claim 1, wherein the fluid outlets comprise both perpendicular fluid outlets and tangential fluid outlets, wherein the perpendicular fluid outlets are positioned such that fluid is delivered out from the at least one fluid channel via the perpendicular fluid outlets in a perpendicular direction to the inner wall and the tangential fluid outlets are positioned such that fluid is delivered out from the at least one fluid channel via the tangential fluid outlet in a tangential direction to the inner wall.

7. The pre-hydrolysis pressure vessel system according to claim 1, wherein the pre-hydrolysis pressure vessel comprises a horizontal bioreactor.

8. The pre-hydrolysis pressure vessel system according to claim 1, wherein the pre-hydrolysis pressure vessel comprises a vertical bioreactor and a horizontal transport screw arrangement for transporting biomass out from the vertical bioreactor towards the material outlet of the pre-hydrolysis pressure vessel, wherein said cleaning arrangement is provided in said horizontal transport screw arrangement.

9. The pre-hydrolysis pressure vessel system according to claim 1, wherein anti-rotation bars provided in the enclosing housing are designed to comprise said at least one fluid channels and said fluid outlets, wherein said anti-rotation bars are provided in the transport screw arrangement for decreasing a risk that the material is rotated inside the enclosing housing.

10. A pre-hydrolysis pressure vessel system comprising:

a material inlet for receiving biomass material to be treated in the pre-hydrolysis pressure vessel system;

a material outlet for expelling treated biomass material out from the pre-hydrolysis pressure vessel system; and a transport screw arrangement comprising:

an enclosing housing; and a transport screw provided in the enclosing housing, said transport screw being configured for transporting biomass material through the enclosing housing towards the material outlet of the pre-hydrolysis pressure vessel system, wherein said enclosing housing comprises a cleaning arrangement, said cleaning arrangement comprising:

at least one elongated fluid channel provided along at least a part of a length (L1) of the enclosing housing, each defined by at least an inner wall of the enclosing housing, wherein each elongated fluid channel comprises a plurality of fluid outlets separated along a length (L2) of the respective fluid channel, and at least one cleaning fluid inlet which is provided through the enclosing housing in fluid connection with the at least one fluid channel whereby a cleaning fluid can be provided into the enclosing housing from outside the enclosing housing, via the cleaning fluid inlet and through the at least one fluid channel and said fluid outlets for cleaning the transport screw and/or the inner wall of the enclosing housing, wherein at least some of the fluid outlets are provided with an opening being at least 10 times wider than its height, and a height of at least some of the fluid outlets is between 0.05-1 mm.

11. A pre-hydrolysis pressure vessel system comprising:

a material inlet for receiving biomass material to be treated in the pre-hydrolysis pressure vessel system;

a material outlet for expelling treated biomass material out from the pre-hydrolysis pressure vessel system; and a transport screw arrangement comprising:

an enclosing housing; and a transport screw provided in the enclosing housing, said transport screw being configured for transporting biomass material through the enclosing housing towards the material outlet of the pre-hydrolysis pressure vessel system, wherein said enclosing housing comprises a cleaning arrangement, said cleaning arrangement comprising:

at least one elongated fluid channel provided along at least a part of a length (L1) of the enclosing housing, each defined by at least an inner wall of the enclosing housing, wherein each elongated fluid channel comprises a plurality of fluid outlets separated along a length (L2) of the respective fluid channel, and at least one cleaning fluid inlet which is provided through the enclosing housing in fluid connection with the at least one fluid channel whereby a cleaning fluid can be provided into the enclosing housing from outside the enclosing housing, via the cleaning fluid inlet and through the at least one fluid channel and said fluid outlets for cleaning the transport screw and/or the inner wall of the enclosing housing, wherein the fluid outlets comprise both perpendicular fluid outlets and tangential fluid outlets, wherein the perpendicular fluid outlets are positioned such that fluid is delivered out from the at least one fluid channel via the perpendicular fluid outlets in a perpendicular direction to the inner wall and the tangential fluid outlets are positioned such that fluid is delivered out from the at least one fluid channel via the tangential fluid outlet in a tangential direction to the inner wall.

* * * * *